(12) United States Patent
Taya (10) Patent No.: US 10,595,950 B2
(45) Date of Patent: Mar. 24, 2020

(54) FERROMAGNETIC SHAPED MEMORY ALLOY NANO-ACTUATOR AND METHOD OF USE

(71) Applicant: University of Washington, Seattle, WA (US)

(72) Inventor: Minoru Taya, Mercer Island, WA (US)

(73) Assignee: University of Washington, Seattle, WA (US)

(*) Notice: Subject to any disclaimer, the term of this patent is extended or adjusted under 35 U.S.C. 154(b) by 272 days.

(21) Appl. No.: 15/569,680

(22) PCT Filed: Apr. 28, 2016

(86) PCT No.: PCT/US2016/029883
§ 371 (c)(1),
(2) Date: Oct. 26, 2017

(87) PCT Pub. No.: WO2016/176509
PCT Pub. Date: Nov. 3, 2016

(65) Prior Publication Data
US 2018/0116744 A1 May 3, 2018

Related U.S. Application Data

(60) Provisional application No. 62/153,857, filed on Apr. 28, 2015, provisional application No. 62/235,377, (Continued)

(51) Int. Cl.
*A61B 34/00* (2016.01)
*A61B 34/30* (2016.01)
(Continued)

(52) U.S. Cl.
CPC ........ *A61B 34/73* (2016.02); *A61B 17/00234* (2013.01); *A61B 34/30* (2016.02);
(Continued)

(58) Field of Classification Search
CPC .......... A61B 34/73; A61B 2017/00867; A61B 2017/00345; A61B 2034/302; A61F 2210/0014
See application file for complete search history.

(56) References Cited

U.S. PATENT DOCUMENTS 5,921,933 A   7/1999   Sarkis et al.
6,231,496 B1  5/2001   Wilk et al.
(Continued)

FOREIGN PATENT DOCUMENTS

WO     01/17611 A1    3/2001
WO     2015/134620    9/2015

OTHER PUBLICATIONS

Asua et al., "Design of a new FSMA-based actuator for nanopositioning applications," Proc. SPIE 8409, Third International Conference on Smart Materials and Nanotechnology in Engineering, vol. 8409 (Apr. 2, 2012) (Year: 2012).*

(Continued)

*Primary Examiner* — Thaddeus B Cox
(74) *Attorney, Agent, or Firm* — Christensen O'Connor Johnson Kindness, PLLC (57) ABSTRACT

Nano-actuators having a helical member formed with a ferromagnetic shape memory alloy (FSMA) are disclosed that are elastically deformable between a compressed state and an expanded state by the application of a magnetic field. The nano-actuators may include a ferromagnetic head portion, that may be formed from the FSMA or from another material. A thin biocompatible external layer provides a platform for attaching a ligand that is selected to bind with a target cell type, for example, a target cancer cell. The nano-actuators are magnetically propelled to the target cells, and oscillated and/or rotated to mechanically damage the target cells to induce apoptosis. The nano-actuators may be (Continued)

formed by electro deposition of the FSMA into a nanohelical template.

20 Claims, 5 Drawing Sheets

Related U.S. Application Data filed on Sep. 30, 2015, provisional application No. 62/298,847, filed on Feb. 23, 2016.

(51) Int. Cl.

| | |
|---|---|
| A61B 17/00 | (2006.01) |
| H01L 41/12 | (2006.01) |
| H01L 41/47 | (2013.01) |
| A61B 34/32 | (2016.01) |
| A61B 90/00 | (2016.01) |
| A61B 18/00 | (2006.01) |
| A61B 34/20 | (2016.01) |
| A61M 31/00 | (2006.01) |

(52) U.S. Cl.
CPC .............. *A61B 34/32* (2016.02); *H01L 41/12* (2013.01); *H01L 41/47* (2013.01); *A61B 2017/00345* (2013.01); *A61B 2017/00526* (2013.01); *A61B 2017/00867* (2013.01); *A61B 2018/0019* (2013.01); *A61B 2018/00577* (2013.01); *A61B 2034/2051* (2016.02); *A61B 2034/302* (2016.02); *A61B 2034/731* (2016.02); *A61B 2090/374* (2016.02); *A61M 31/002* (2013.01); *A61M 2210/1007* (2013.01)

(56) References Cited

U.S. PATENT DOCUMENTS

| | | | |
|---|---|---|---|
| 6,470,220 | B1 | 10/2002 | Kraus, Jr. et al. |
| 6,514,481 | B1 | 2/2003 | Prasad et al. |
| 2005/0001367 | A1 | 1/2005 | Taya et al. |
| 2006/0206140 | A1* | 9/2006 | Shaolian .......... A61B 17/12022 606/200 |
| 2007/0196281 | A1 | 8/2007 | Jin et al. |
| 2007/0236314 | A1* | 10/2007 | Taya .......... F04B 9/06 335/220 |
| 2007/0282425 | A1 | 12/2007 | Kleine et al. |
| 2008/0004692 | A1* | 1/2008 | Henson ............ A61B 17/12022 623/1.18 |
| 2008/0117006 | A1 | 5/2008 | Claeys et al. |
| 2008/0302024 | A1 | 12/2008 | Browne et al. |
| 2009/0155284 | A1* | 6/2009 | Cao .......... C07K 16/22 424/145.1 |
| 2010/0241076 | A1 | 9/2010 | Rush et al. |
| 2010/0301857 | A1 | 12/2010 | Hyde et al. |
| 2012/0035437 | A1 | 2/2012 | Ferren et al. |
| 2013/0116621 | A1 | 5/2013 | Park et al. |
| 2015/0238281 | A1* | 8/2015 | Alauddin .............. A61C 7/006 433/11 |

OTHER PUBLICATIONS

International Search Report and Written Opinion dated Aug. 12, 2016, issued in corresponding Application No. PCT/US2016/29883, filed Apr. 28, 2016, 7 pages.
Shingubara, Shoso, "Fabrication of Nanomaterials Using Porous Alumina Templates," Journal of Nanoparticle Research 5:17-30, 2003, pp. 17-30.
Tottori, Soichiro, et al., "Wireless Actuation of Micro/Nanorobots for Medical Applications," in D.J. Lockwood (ed.), Nanomedicine, Nanostructure Science and Technology, Springer, New York, 2014, pp. 171-189.
Abbott, J.J., et al., "How Should Microrobots Swim?" International Journal of Robotics Research 28(11-12):1434-1447, Dec. 2009.
Abbott, J.J., et al., "Modeling Magnetic Torque and Force for Controlled Manipulation of Soft-Magnetic Bodies," IEEE Transactions on Robotics 23(6):1247-1252, Dec. 2007.
Allenstein, U., et al., "Fe-Pd Based Ferromagnetic Shape Memory Actuators for Medical Applications: Biocompatibility, Effect of Surface Roughness and Protein Coatings," Acta Biomaterialia 9(3):5845-5853, Mar. 2011.
Andarawis-Puri, N., et al., "Temporal Effect of In Vivo Tendon Fatigue Loading on the Apoptotic Response Explained in the Context of Number of Fatiue Loading Cycles and Initial Damage Parameters," Journal of Orthopaedic Research 32(9):1097-1103, Sep. 2014.
Cheng, G., et al., "Micro-Environmental Mechanical Stress Controls Tumor Spheroid Size and Morphology by Suppressing Proliferation and Inducing Apoptosis in Cancer Cells," PloS One 4(2):e4632, Feb. 2009, 11 pages.
"Design of Bio-Actuator for Medical Treatment Based on Ferromagnetic Shape Memory Alloy Helical Spring," UW Tech Transfer, UW Ref# 7598D, Dec. 18, 2007, <http://depts.washington.edu/uwc4c/webform_uploader/new/7598.pdf>, 1 page.
Gajbhiye, N.S., et al., "Synthesis of Self-Assembled Monodisperse 3 nm FePd Nanoparticles: Phase Transition, Magnetic Study, and Surface Effect," Journal of Applied Physics 104(12):123906-1-123906-7, Dec. 2008.
Gao, J., et al., "Preconditioning Effects of Physiological Cyclic Stretch on Pathologically Mechanical Stretch-Induced Alveolar Epithelial Cell Apoptosis and Barrier Dysfunction," Biochemical and Biophysical Research Communications 448(3):342-348, Jun. 2014.
Haehnel, V., et al., "Electrodeposition of $Fe_{70}Pd_{30}$ Nanowires From a Complexed Ammonium—Sulfosalicylic Electrolyte With High Stability," Electrochemistry Communications 12(8):1116-1119, Aug. 2010.
Kong, D., et al., "Static Mechanical Stress Induces Apoptosis in Rat Endplate Chondrocytes Through MAPK and Mitochondria-Dependent Caspase Activation Signaling Pathways," PLoS One 8(7):e69403, Jul. 2013, 10 pages.
Liang, Y., et al. "Design of Membrane Actuator Based on Ferromagnetic Shape Memory Alloy Composite for Synthetic Jet Applications," Sensors and Actuators A: Physical 125(2):512-518, Jan. 2006.
Liang Y., et al., "Design of the Inchworm Actuator Based on the Ferromagnetic Shape Memory Alloy Composite," Smart Materials and Structures 21(11):115005, Nov. 2012, 9 pages.
Liang, Y., et al., "Model Calculation of 3D-Phase Transformation Diagram of Ferromagnetic Shape Memory Alloys," Mechanics of Materials 38(5-6):564-570, May-Jun. 2006.
Lien, S.-C. et al. "Mechanical Regulation of Cancer Cell Apoptosis and Autophagy: Roles of Bone Morphogenetic Protein Receptor, Smad1/5, and p38 MAPK," Biochimica et Biophysica Acta 1833(12):3124-3133, Dec. 2013.
Ma, Y., et al., "Biocompatibility of Single Crystalline Fe70Pd30 Ferromagnetic Shape Memory Films," Applied Physics Letters 96(21):213703, May 2010, 3 pages.
Masuda, H., and K. Fukuda, "Ordered Metal Nanohole Arrays Made by a Two-Step Replication of Honeycomb Structures of Anodic Alumina," Science 268(5216):1466-1468, Jun. 1995.
Mathieu, J.-B., and S. Martel, "Steering of Aggregating Magnetic Microparticles Using Propulsion Gradients Coils in an MRI Scanner," Magnetic Resonnance in Medicine 63:1336-1345, 2010.
Mayr, M., et al., "Biomechanical Stress-Induced Apoptosis in Vein Grafts Involves p38 Mitogen-Activated Protein Kinases," The FASEB Journal 15:261-270, Feb. 2000.
Murray, S.J., et al., "6% Magnetic-Field-Induced Strain by Twin-Boundary Motion in Ferromagnetic Ni—Mn—Ga," Applied Physics Letters 77(6):886-888, Aug. 2000.
Ogiue-Ikeda, M., et al., "A New Method to Destruct Targeted Cells Using Magnetizable Beads and Pulsed Magnetic Force," IEEE Transaction on Nanobioscience 2(4):262-265, Dec. 2003.
Pondman, K.M., et al., "Magnetic Drug Delivery With FePd Nanowires," Journal of Magnetism and Magnetic Materials 380:299-306, 2015.

(56) References Cited

OTHER PUBLICATIONS

Pouponneau, P., et al., "Co-Encapsulation of Magnetic Nanoparticles and Doxorubicin Into Biodegradable Microcarriers for Deep Tissue Targeting by Vascular MRI Navigation," Biomaterials 32(13):3481-3486, May 2011.

Pouponneau, P., et al., "Therapeutic Magnetic Microcarriers Guided by Magnetic Resonance Navigation for Enhanced Liver Chemoembilization: A Design Review," Annals of Biomedical Engineering 42(5):929-939, May 2014.

Purcell, E.M., "Life at Low Reynolds Number," American Journal of Physics 45(1):3-11, Jan. 1977.

Purcell, E.M., "The Efficiency of Propulsion by a Rotating Flagellum," Proceedings of the National Academy of Sciences of the USA (PNAS) 94:11307-11311, Oct. 1997.

Servant, A., et al., "Controlled In Vivo Swimming of a Swarm of Bacteria-Like Microrobotic Flagella," Advanced Materials 27(19):2981-2988, May 2015.

Taya, M., et al., "Development of Ferromagnetic Shape Memory Alloys Based on FePd Alloy," APCFS & ATEM Japan Society of Mechanical Engineers, Materials & Mechanics Division, Oct. 20-22, 2001, 10 pages.

Wada, T., and M. Taya, "Spring Based Actuators," Proceedings of SPIE on Smart Structures and Materials, San Diego, Mar. 17-21, 2002, vol. 4699, pp. 294-302.

Wu, Y., et al., "Composite Mesostructures by Nano-Confinement," Nature Materials 3:816-822, Nov. 2004.

Yamamoto, T., et al., "Magnetic Field-Induced Reversible Variant Rearrangement in Fe—Pd Single Crystals," Acta Materialia 52(17):5083-5091, Oct. 2004.

Zhang, L., et al., "Artificial Bacterial Flagella: Fabrication and Magnetic Control," Applied Physics Letters 94(6):064107-1-064107-3, Feb. 2009.

Zhao, D. et al., "Continuous Mesoporous Silica Films With Highly Ordered Large Pore Structures," Advanced Materials 10(16):1380-1385, 1998.

\* cited by examiner

FERROMAGNETIC SHAPED MEMORY ALLOY NANO-ACTUATOR AND METHOD OF USE

CROSS-REFERENCES TO RELATED APPLICATIONS

This application claims the benefit of U.S. Provisional Patent Application No. 62/153,857, filed on Apr. 28, 2015, which is hereby incorporated by reference in its entirety, and claims the benefit of U.S. Provisional Patent Application No. 62/235,377, filed Sep. 30, 2015, which is hereby incorporated by reference in its entirety, and claims the benefit of U.S. Provisional Patent Application No. 62/298,847, filed Feb. 23, 2016, which is hereby incorporated by reference in its entirety.

BACKGROUND

The targeting and removal or destruction of malignant cells in a body is an ongoing battle in the war against cancer. As an option to the surgical removal of malignant cells, modern medical advances have developed treatments, such as chemical and radiation treatments, that are designed to induce in situ programmed cell death in malignant cells. Programmed cell death refers generally to the self-destruction of cells (cell suicide), for example, by apoptosis, autophagy, and necroptosis. References herein to apoptosis will be understood to apply to other forms of programmed cell death. The challenge in existing procedures to induce apoptosis is to achieve acceptable levels of malignant cell death, without undue collateral damage to healthy cells.

Apoptosis is distinguished from necrosis. Necrosis occurs, for example, when a cell is sufficiently damaged by an external factor, such as poison, a bodily injury, or an infection. When cells die from necrosis, it may cause inflammation that can cause further damage to the body. Apoptosis, on the other hand, is relatively less stressful to the body, following a controlled, predictable routine. When the cell is induced to undergo programmed cell death proteins called caspases (cysteine-aspartic proteases, cysteine aspartases, or cysteine-dependent aspartate-directed proteases) break down the cellular components needed for survival, and spur production of deoxyribonuclease enzymes known as DNases, which destroy the DNA in the nucleus of the cell. Apoptosis is a natural and ongoing process essential to human development.

Cells that go through apoptosis die or self-destruct in response to signals within the body. For example, when cells recognize viruses and gene mutations, they may initiate programmed cell death to prevent the damage from spreading. When cells are under stress, apoptosis can occur. Anti-cancer drugs and radiation, for example, typically work by triggering apoptosis in diseased cells.

If a cell sustains irreparable internal damage the cell will initiate apoptosis. In particular, a damaging mechanical disruption to a cell can induce the cell to initiate apoptosis. It would be beneficial if malignant cells in a body could be targeted and selectively mechanically agitated to induce damage sufficient to cause the target cell to initiate programmed cell death without rendering the cells necrotic. Nano-actuators and methods are disclosed herein to initiate such apoptosis to remove cancer cells. In particular, the disclosed methods provide a treatment that does not require irradiation or poisoning of the body (or reduces the amount of irradiation or poisoning) thereby avoiding or mitigating unwanted collateral health effects that may be caused by such treatments.

The Taya group at the University of Washington has developed a number of macro-scale ferromagnetic shape memory alloy (FSMA) actuator. One of the FSMA actuators is formed from an iron-palladium alloy (FePd) as a helical spring. The FePd spring can be actuated or compressed using an externally applied magnetic gradient field. The mechanism of the actuation of the FePd spring is believed to be a chain-reaction sequence wherein (i) the applied magnetic gradient field induces (ii) a magnetic force, which (iii) results in a stress-induced diffusionless martensite phase transformation in the FePd, and (iv) as a result of the phase change, the Young's modulus of the spring is reduced, enabling a large deformation in the spring. The above sequential chain-reaction takes place within a very short time.

Actuators are relatively simple mechanical components that are often incorporated into more complex mechanical systems. Shape memory alloys are alloys that may transition or transform between two different phases. Large (macro-scale) linear actuators having a helical spring formed at least partially from an FSMA are known in the art. For example, one of the present inventors has disclosed an FSMA spring actuator in U.S. Pat. No. 7,104,056, to Taya et al., which is hereby incorporate by reference in its entirety. The disclosed spring actuator includes an FSMA coil, a hybrid magnetic trigger including both a permanent magnet and an electromagnet, and a yoke configured to couple magnetic flux from the magnet to the spring.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A nano-actuator includes a ferromagnetic head and a compliant helical portion extending from the head formed in part from a ferromagnetic shape memory alloy, and configured to be elastically compressible with an external magnetic field, and to expand when the magnetic field is removed.

In an embodiment at least the head includes a biocompatible layer, for example an oxide layer.

In an embodiment the head includes a tapered portion.

In an embodiment the ferromagnetic shape memory alloy is an iron-palladium alloy, for example $Fe_{70}Pd_{30}$.

In an embodiment, a ligand selected to bind with a target cell is retained on the oxide layer.

In an embodiment the nano-actuator includes a second head disposed on an opposite end of the helical member.

A method for the targeted treatment of malignant cells includes providing a plurality of nano-actuators comprising helical members formed from a ferromagnetic shape memory alloy, applying a ligand to a surface of the nano-actuators that is selected to bind with a receptor of the malignant cells, injecting the nano-actuators into a body containing the malignant cells, magnetically propelling the nano-actuators toward malignant cells such that at least some of the nano-actuators bind to target cells, and cycling the helical members between an expanded state and a compressed state by applying an oscillating magnetic field, wherein the magnetic field in configured to induce a phase transformation in the shape memory alloy.

In an embodiment the ferromagnetic shape memory alloy comprises an iron-palladium alloy, for example $Fe_{70}Pd_{30}$.

In an embodiment the plurality of nano-actuators have a ferromagnetic head portion fixed on an end of the helical member.

In an embodiment the head portion is iron or an iron alloy.

In an embodiment the head portion is an iron-palladium alloy.

In an embodiment the head portion includes a biocompatible oxide layer.

In an embodiment the nano-actuator also has a second ferromagnetic head portion disposed opposite the first head portion.

In an embodiment the first head portion has a bullet shape comprising a tapered portion and a cylindrical portion.

In an embodiment the nano-actuators are propelled towards the malignant cells with a rotating magnetic field that is configured to spin the nano-actuators about an axis of the helical member.

A nano-robotic system includes a magnetic field generator configured to selectably and controllably generate an oscillating magnetic field, a gradient magnetic field, and a rotating magnetic field; a controller functionally connected to the magnetic field generator and operable to control the magnetic field produced by the magnetically field generator; and a plurality of nano-actuators, each nano-actuator comprising a first head portion formed from a ferromagnetic material and a helical portion extending from the head portion, the helical portion comprising a compliant ferromagnetic shape memory alloy, wherein the helical portion is configured to be elastically compressible by an external magnetic field generated by the magnetic field generator, and to expand when the external magnetic field is removed.

In an embodiment the oscillating magnetic field is configured to induce a martensitic phase transformation in the ferromagnetic shape memory alloy.

In an embodiment the ferromagnetic shape memory alloy is an iron-palladium alloy.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Tiny medical robots configured to be injected into a body and having a characteristic dimension on the order of one to tens of microns have been proposed in the literature as candidates for use in vivo use to deliver drugs to a particular location in the body. See, for example, Fountain, Thomas W R, Prem V. Kailat, and Jake J. Abbott. "Wireless Control of Magnetic Helical Microrobots Using a Rotating-Permanent-Magnet Manipulator." Robotics and Automation (ICRA), 2010 IEEE International Conference on. IEEE, 2010 ("Fountain et al."), which is hereby incorporated by reference in its entirety. However, the micro-robots disclosed are contemplated as delivery devices for delivering particular (often toxic) drugs to desired locations in the body.

In the low Reynold's number flow (Stoke's flow) associated with the micro-robots discussed in Fountain et al., as well as the nano-actuators disclosed in the present application, a helical configuration provides advantages associated with propelling the devices through biological fluids. Helical members rotating about the longitudinal axis is an efficient method of propelling the helical members in Stoke's flow, and the direction of propulsion can be reversed by reversing the direction of rotation, without requiring the helical members themselves to be re-oriented in the flow.

Figure 1A:
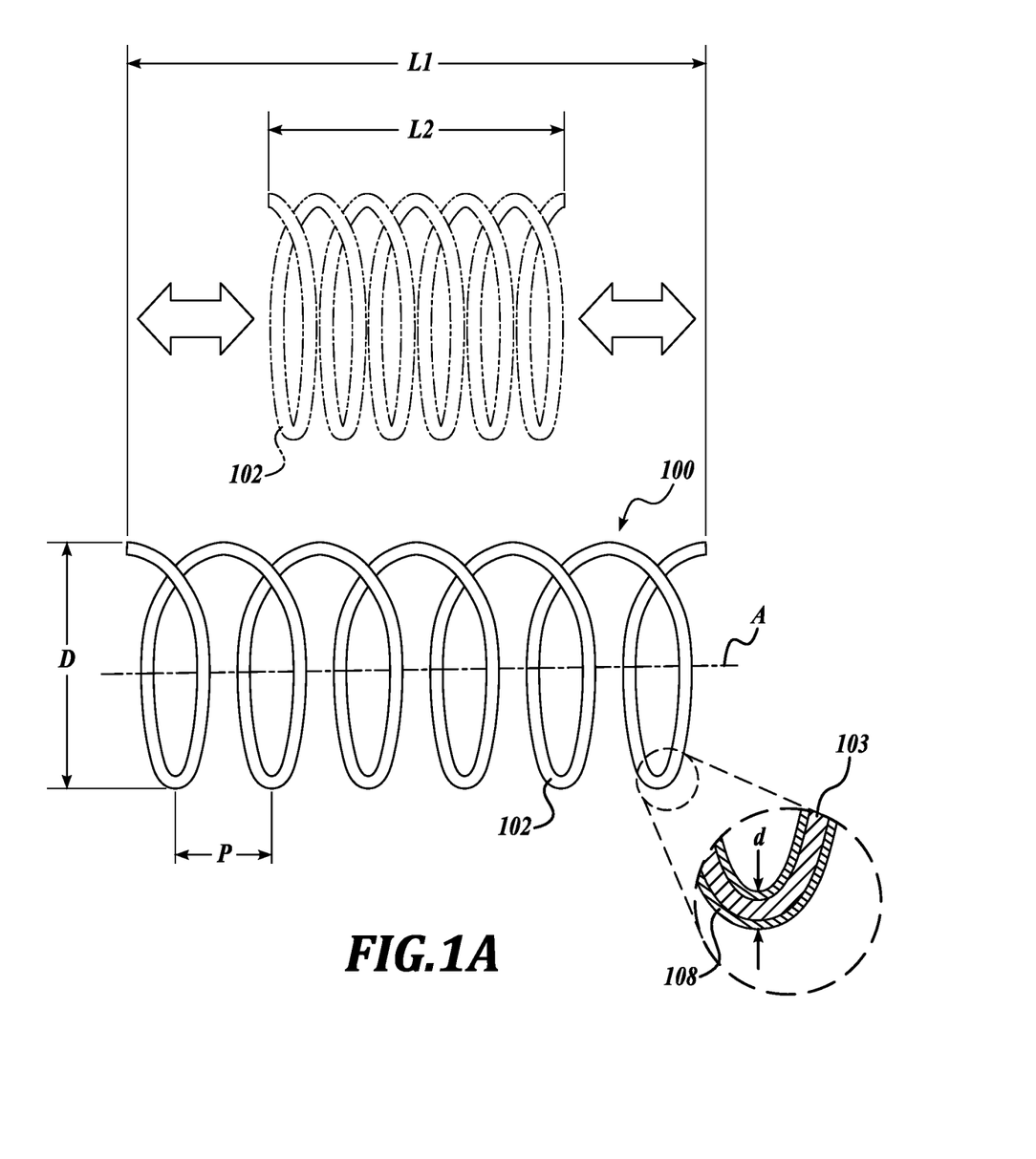
FIG. 1A illustrates schematically a first embodiment of a nano-actuator in accordance with the present invention also showing a detail sectional view of a portion of the nano-actuator, shaped as a helical member.

A first exemplary embodiment of a nano-actuator 100 in accordance with the present invention is shown in FIG. 1A, which also shows a sectional view of a portion of the nano-actuator 100. The nano-actuator 100 in this embodiment is an elongate helical member 102 having ferromagnetic properties. The nano-actuator 100 can therefore be manipulated with a magnetic field, as discussed in more detail below.

The nano-actuator 100 has an elastic ferromagnetic shape memory alloy (FSMA) core 103. For example, the FSMA core 103 may be formed from an iron-palladium FSMA. The FSMA core 103 is selected such that the helical member 102 is elastically compressible in the axial direction (axis A) of the helical member 102. In FIG. 1A the nano-actuator 100 is shown in an expanded state having a length L1, and shown in broken line in a compressed state having a length L2. In an exemplary embodiment the helical member 102 has an expanded length L1 between 1 micrometer and 100 nm, and in some embodiments several hundred nanometers. In an exemplary embodiment the helical member 102 has a spring diameter D between 20 nm and 100 nm, for example, 60 nm. In an exemplary embodiment the helical member 102 has a wire diameter d between about 5 nm and 30 nm, for example, 10 nm. In an exemplary embodiment the angle of inclination of the helical coils is between 3 degrees and 20 degrees, for example, about 13 degrees, with a spring pitch P between 1 nm and 20 nm, for example, about 5 nm. These dimensions are exemplary ranges, and are not intended to be limiting.

It is well known that placing an FSMA in a suitable magnetic field can induce a martensite phase transformation. A martensite transformation in the cores 103 of the actuators 100 will reduce the Young's modulus in the FSMA. The diffusionless transformation allows the helical member to undergo a relatively large contraction in the magnetic field. Therefore, the nano-actuator 100 may be selectively moved between an expanded state having the length L1 and a compressed state having the length L2, by selectively controlling an external magnetic field (both a constant magnetic field and also a gradient magnetic field). For example, an intermittent or oscillating magnetic field can be used to cause the nano-actuator to oscillate between lengths L1 and L2.

The FSMA core 103 is coated with a thin biocompatible layer 108 (for example, a few nanometers) for example, an oxide layer. In a current embodiment the biocompatible layer 108 comprises polyethylene glycol (PEG, also known as polyethylene oxide) and/or an iron oxide layer such as $Fe_3O_4$. Other biocompatible layer materials are known in the art, and the selection of a suitable biocompatible layer is believed to be within the skill in the art, based on the present disclosure.

Figure 1B:
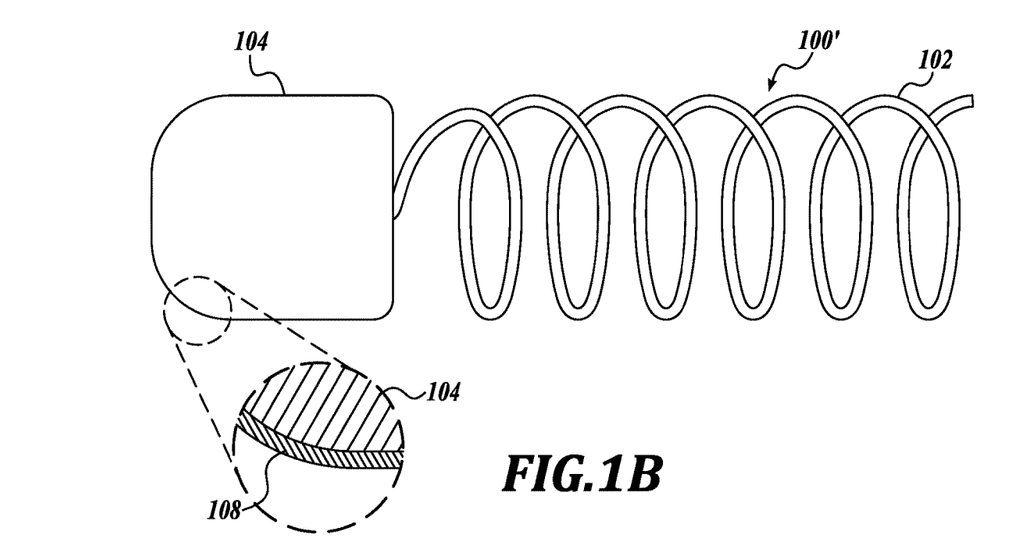
FIG. 1B illustrates a second embodiment of a nano-actuator in accordance with the present invention, including a head portion on one end of the helical member shown in FIG. 1A and showing a detail sectional view of the head portion.

A second exemplary embodiment of a nano-actuator 100' in accordance with the present invention is shown in FIG. 1B. In this embodiment, the nano-actuator 100' includes a helical member 102 as described above with reference to FIG. 1A. The helical member 102 includes an FSMA core 103, and is elastically compressible along its axis A.

The nano-actuator 100' further includes a head portion 104 that is co-formed or fixed to one end of the helical member 102. The head portion 104 is formed from a ferromagnetic material. In one embodiment the head portion 104 is formed from the same FSMA as the helical member 102. Alternatively, the head portion 104 may be formed from iron, or from another alloy of iron. The head portion 104 also has a biocompatible outer layer 108, for example, an oxide such as polyethylene glycol. The head portion 104 provides a surface for applying any desired biological components, for example, ligands that are selected to form a complex with a binding partner or receptor on a target cell, and/or chemical agents selected to disrupt the target cell. The head portion 104 may also increase the contraction of the helical member 102, and may improve the ability to magnetically manipulate the orientation and propulsion of the nano-actuator 100'.

Figure 1C:
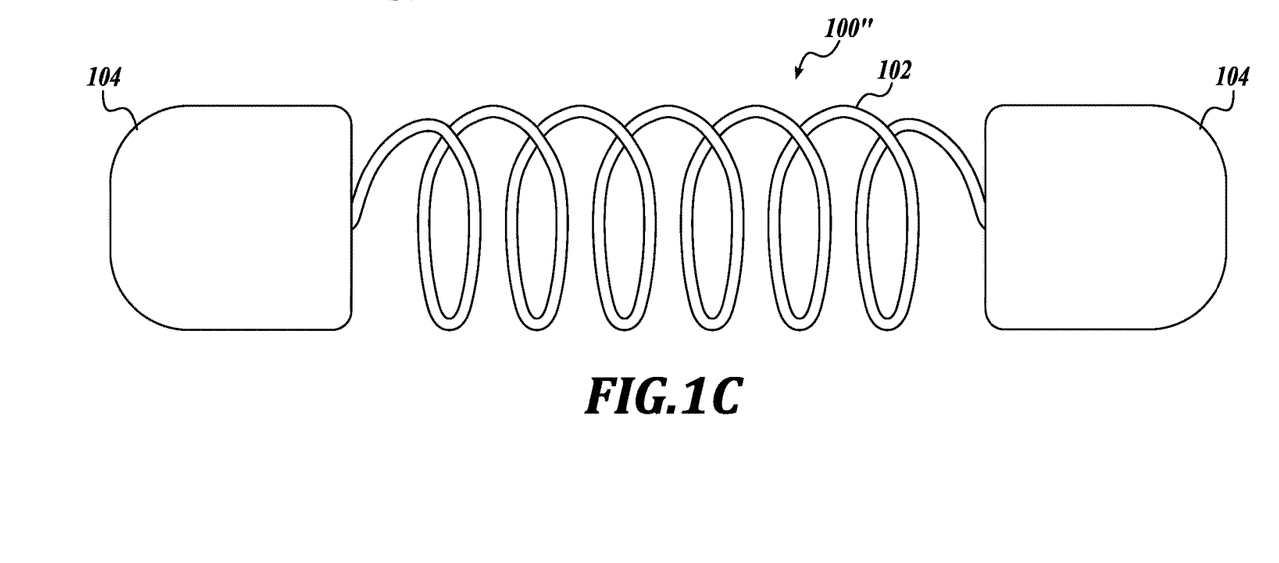
FIG. 1C illustrates schematically a third embodiment of a nano-actuator in accordance with the present invention, including head portions on both ends of the helical member shown in FIG. 1A.

A third embodiment of a nano-actuator 100" in accordance with the present invention is shown in FIG. 1C. In this embodiment, the nano-actuator 100" includes a helical member 102, with head portions 104 on both ends of the helical member 102.

Figure 2A:
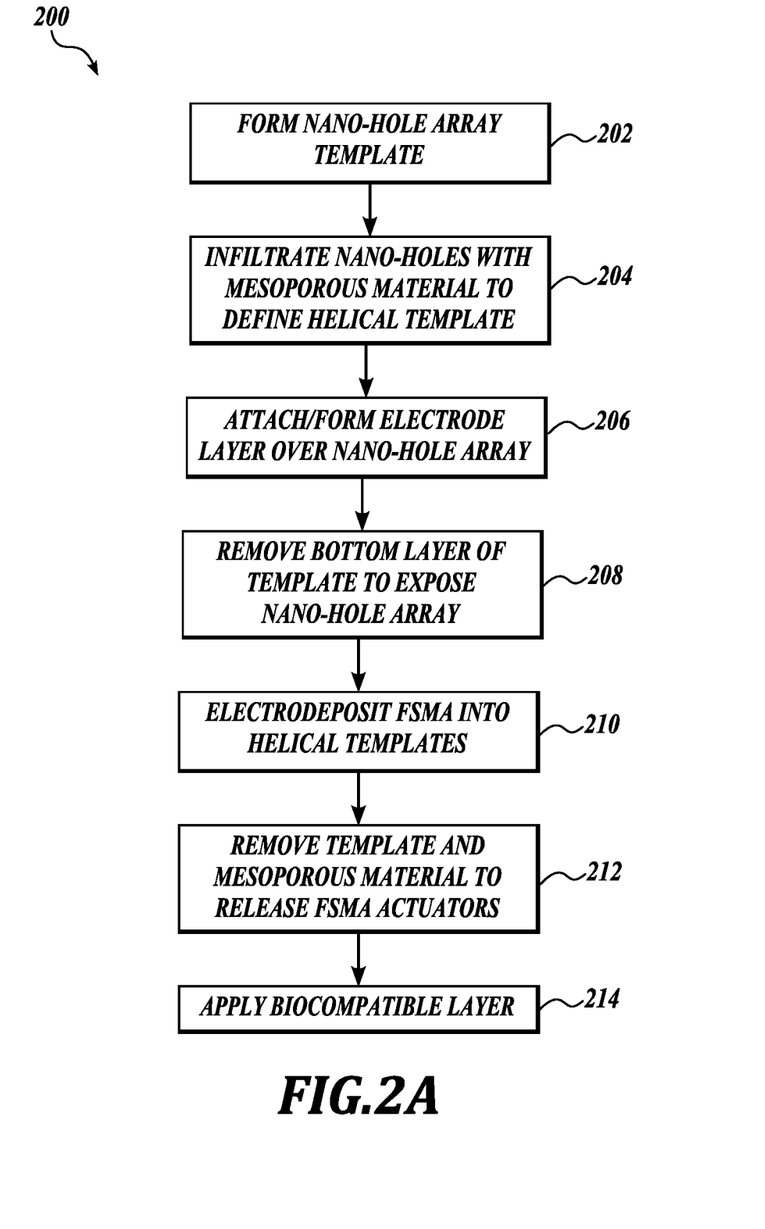
FIG. 2A is a flow chart showing a method in accordance with the present invention for producing the nano-actuator shown in FIG. 1A.
Figure 2B:
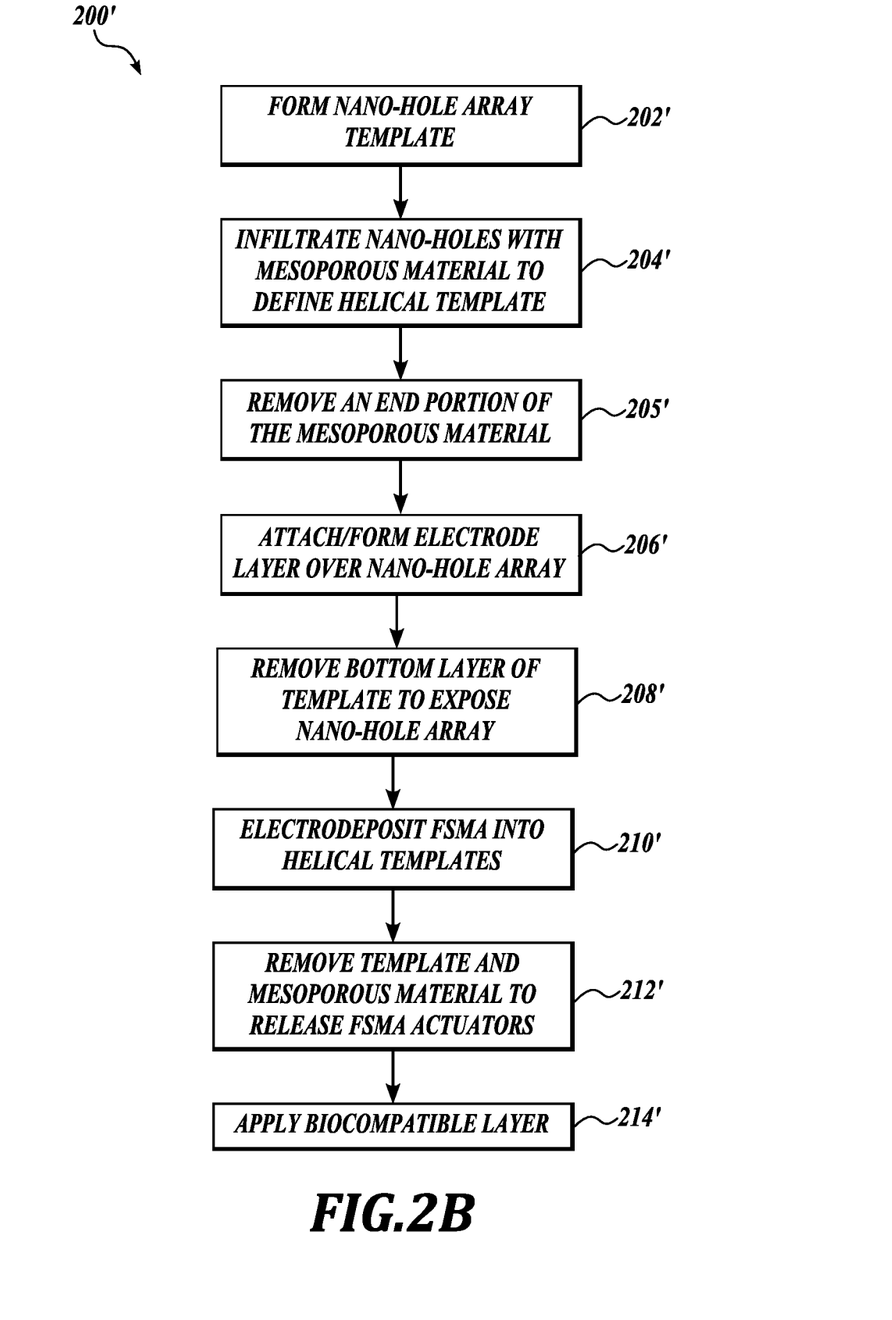
FIG. 2B is a is a flow chart showing a method in accordance with the present invention for producing the nano-actuator shown in FIG. 1B.

An exemplary method 200 of making the nano-actuator 100 shown in FIG. 1A, i.e., without a head portion, is shown in FIG. 2A. An exemplary method 200' of making the nano-actuator 100', i.e., with a head portion 104 is shown in FIG. 2B.

In both methods 200, 200', a nano-hole array template 202, 202' is first formed. For example, a nano-hole array template may comprise a porous alumina film formed by anodic oxidation of aluminum. A porous alumina film may be formed by a well-known two-step anodization process. See, for example, Shingubara, Shoso, "Fabrication of nano-materials using porous alumina templates," Journal of Nanoparticle Research 5.1-2 (2003): 17-30, which is hereby incorporated by reference in its entirety. To obtain a particular hole diameter, an optional hole-widening step may be conducted in a 5 wt % $H_3PO_4$ aqueous solution. In exemplary embodiments, pore diameters in the range to 20 nm to 80 nm have been obtained.

The nano-holes in the array are then infiltrated with a mesoporous material 204, 204' selected to define a helical template within the nano-holes. An exemplary mesoporous material suitable for the present application is mesoporous silicon dioxide ($SiO_2$). In an exemplary embodiment, the mesoporous silica is synthesized by sol-gel dip coating method. For example, in one embodiment the molar ratio of the dip coating solution is 1 tetraethyl orthosilicate:0.0096 poly(ethylene oxide)-poly(propylene oxide)-poly(ethylene oxide) (PEO-PPO-PEO) copolymers:6 H2O:8.8 ethanol: 0.001 HCl.

For example, the thin biocompatible layer on the surface of the nano-actuator may be applied by an ozonation process, e.g., by submerging the nano-actuators in a solution that is heated to an intermediate temperature while the solution is mixed with ozone bubbles.

In the method 200' for producing a nano-actuators 100' with a head portions 104, some of the mesoporous silica is removed 205' from the proximal end of the nano-hole array to accommodate formation of the head portion 104.

In both methods 200, 200', an electrode is then formed on the nano-hole array 206, 206'. In a current embodiment, the electrode layer is made of gold, a conducting polymer, and an indium tin oxide (ITO) substrate. For example, in this embodiment a gold layer is formed by sputtering gold onto the $SiO_2$ infiltrated porous anodized alumina. An ITO/glass layer is then attached to the gold layer with a silver epoxy.

A layer of material is then removed from the opposite end of the nano-hole array template 208, 208', opening the nano-holes. The selected FSMA is then electro deposited into the helical nano-hole templates 210, 210'. When producing the nano-actuators 100' with a head portion 104, the electro deposition step 210' also forms the head portions in the end of the nano-holes from which a portion of the mesoporous material was removed. The electro deposition may be performed in two steps if the head portion is a different ferromagnetic material than the helical portion.

The nano-hole array template and mesoporous material are then removed 212, 212', for example, by dissolving the template, to release the nano-actuators 100, 100'.

During the electro deposition of the FSMA, it is desirable to provide spatially homogeneous deposition of the FSMA into the nano-helical holes in the porous alumina/$SiO_2$ template. In exemplary embodiments of the iron palladium alloy wherein the alloy comprises an iron mass fraction of x, (i.e., $Fe_xPd_{(1-x)}$), x in the range of 0.5-0.8 produces a helical spring having desirable elasticity. An iron mass fraction of about 0.7 (e.g., $Fe_{70}Pd_{30}$) is currently believed to be optimal for some applications. It was discovered that using the FSMA material produces a nano-spring that can be elastically deformed with magnetic fields, and will return to an undeformed condition when the magnetic field is removed.

For example, in one embodiment of the electro deposition process the working electrode is the porous alumina/$SiO_2$ template with the gold electrode. A platinum counter electrode and a silver/silver chloride reference electrode were used with an electrolyte made of PdCl, $Fe_2(SO_4)_3$, $NH_3$, $C_7H_6O_6S$, $(NH_4)_2SO_4$ and $H_2SO_4$ under pH=5.

In another method a DC pulse electro deposition method was found to be effective for controlling the atomic composition percentage of the FSMA alloy and to ensure continuous filling of the FePd nano-helices. The composition of the FePd alloy is adjusted by varying the applied potential voltage to the working electrode. The applied potential to the working electrode was typically in the range of −0.9V to about −1.4V.

The nano-actuators 100, 100' are then provided with a biocompatible layer 108 over the nano-actuator, or a portion of the nano-actuator 214, 214'. The bio-compatible layer facilitates attaching organics to the nano-actuators 214, 214', for example, components to allow the nano-actuators to be in suspension in a bodily fluid, ligands selected to engage receptors or binding partners on the target cells, and/or other chemical agents to be transported to the target cells. The biocompatible layer 108 may comprise, for example, an oxide, for example, an iron oxide such as $Fe_3O_4$.

It may be desirable to contour or taper the shape of the head portion 104, for example to produce a bullet-shaped head portion 104 as illustrated in FIG. 1B, for example, to reduce drag on the nano-actuator 100'. This can be accomplished, for example, by etching the template for a period of time, for example, with 0.1M NaOH, before releasing the nano-actuators. In another embodiment not shown the head portion is conical or includes a frustoconical portion.

The novel DC pulse technique for forming the nano-helical springs 102 was found to be preferable over conventional AC electroplating. In particular, the DC pulse method was found to be very effective to control the desired stoichiometry of the alloy. Although nano-helical members may be formed using conventional AC electro deposition for non-alloy members, it was found to be less effective for alloy nano-helical members. Selection of appropriate electrodes and electro deposition parameters are within the ordinary skill in the art.

The length of the helical portion 102 of the nano-actuators 100, 100' is limited by the thickness of the template, and also depends on the total deposition time. If the nano-actuator 100' includes a head portion 104, the ratio of the length of the head portion 104 and the helical coil 102 is determined by the amount of mesoporous material removed from the template prior to electro deposition. However, the method may be modified to produce longer actuators 100', with the head portion 104 and the helical member 102 connected in series by adding another etching step prior to the electro-deposition step, to create another cylindrical pore in the template. The added etching step may be reactive ion etching, for example.

The nano-actuator 100, 100' shown in FIGS. 1A and 1B are a new type of device that can be actuated by a constant magnetic field or by a gradient magnetic field. The FSMA, for example, $Fe_{70}Pd_{30}$, is paramagnetic, and can be magnetized under a modest magnetic field. The nano-actuator 100 may be formed with, or without, a solid head portion 104, and either embodiment may be suitable for particular applications. For actuators 100' with a head portion 104, the head portion may be formed from the same FSMA as the helical member 102, or it may be forms as iron, or from any suitable iron alloy or ferromagnetic material.

Figure 3:
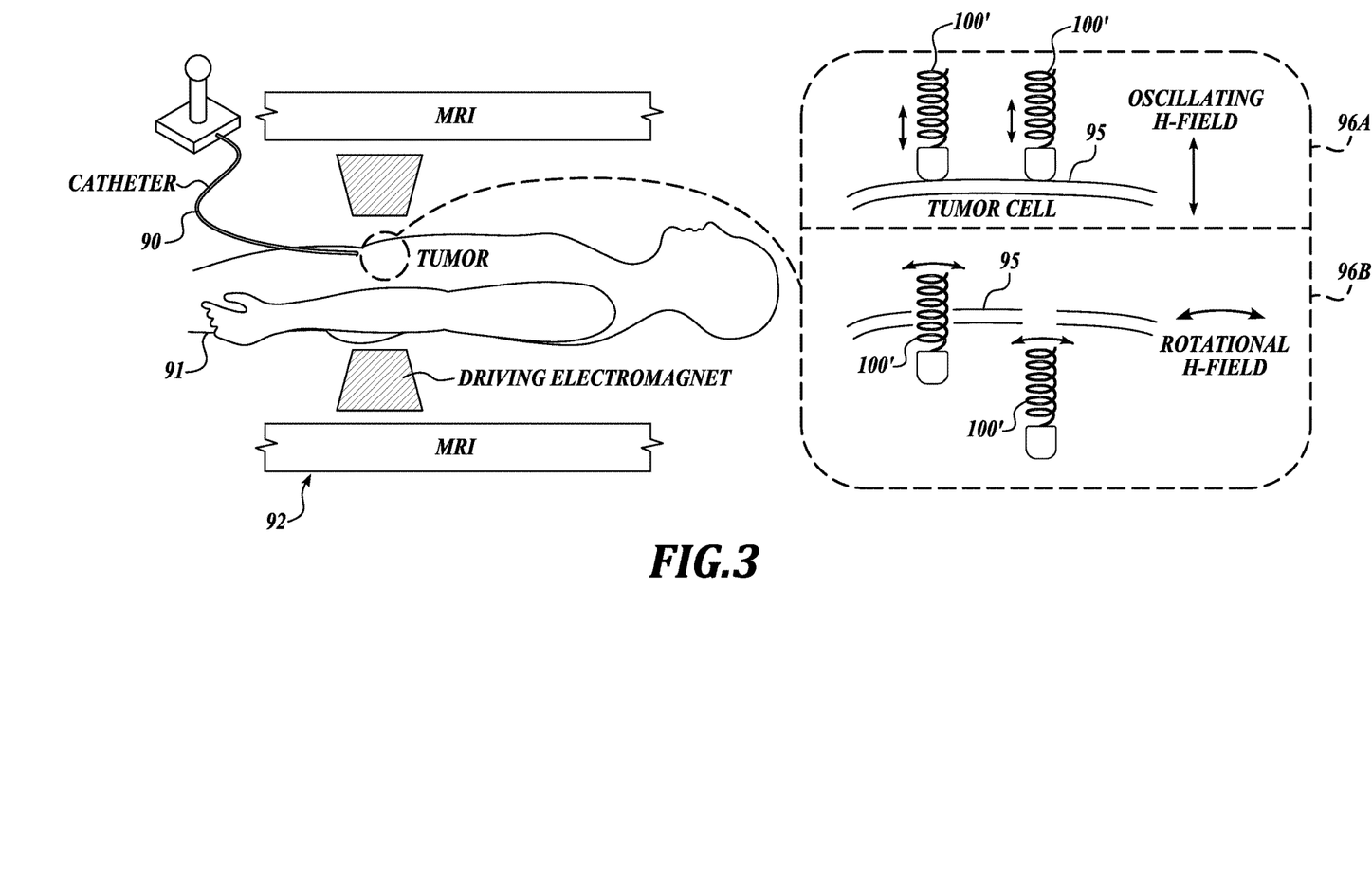
FIG. 3 illustrates schematically a method for using the nano-actuators shown in FIGS. 1A and 1B.

In embodiments of methods in accordance with the present disclosure, a plurality of nano-actuators 100 or 100', are urged towards target cells in a body, for example, malignant cells, and activated to induce programmed cell death in the target cell (see, FIG. 3).

A method of using the nano-actuators 100, 100' disclosed above as untethered robots, for example, for the treatment of malignant cells in a body, will now be described. A ligand selected for a particular receptor or binding partner on the target malignant cells is affixed to at least a portion of the biocompatible surface of the nano-actuators 100, 100'. Optionally, one or more additional biological or chemical agents that are directed to affecting the target cells may also be applied to the biocompatible surface of the nano-actuators, for delivery to the target cells.

In use, the nano-actuators 100, 100' act as untethered nano-robots that are deployed into a body. The motions of the untethered robots 100, 100' are controlled by dynamically applied magnetic fields that direct the nano-actuators 100, 100' from a catheter to the target cells, such that the ligands can engage binding sites on the target cells, and then control the motions of the nano-actuators 100, 100' at the target cells. As is well-known, some ligand/binding site combinations will bind the ligand to the membrane of the cell, and other ligand/binding site combinations will allow the ligand (and therefore the nano-actuator) to partially or fully pass though the membrane into the cell. The nano-actuators 100, 100' are suitable for use in either configuration.

When sufficient nano-actuators 100, 100' have engaged with target cells (which may be estimated by providing sufficient time, or using imaging technologies such as MRI) a dynamic magnetic field is applied that causes the helical elements 102 to vibrate between the expanded length L1 shown in FIG. 1A and the contracted length L2. Optionally, a rotating magnetic field may be applied that is configured to cause the nano-actuators 100, 100' to rotate about their respective axes A.

A method of using the nano-actuators 100, 100' is illustrated in FIG. 3. In this embodiment, plural nano-actuators 100, 100' are deployed in a conventional manner, for example, using a catheter 90, to a location in the body 91 near the target malignant cells (not shown). The body 91 is placed within an apparatus capable of controllably generating magnetic fields that extend into the body 91. It is contemplated that a magnetic resonance imaging (MRI) system 92 (shown schematically) would be suitable, although a custom apparatus directed specifically to the control of the nano-actuators 100, 100' may alternatively be used.

The apparatus, for example an MRI apparatus, will include a magnetic field generator, as is well-known in the art, configured to selectively and controllably generate a magnetic field, and a controller functionally connected to the magnetic field generator to control the magnetic field. The magnetic field generator is preferably configured to selectively produce an oscillating magnetic field, an intermittent constant magnetic field, a gradient magnetic field, and a rotating magnetic field. For example, an apparatus to generate optimum static and dynamic magnetic fields may include 3D Helmholtz coils (that may be installed in an MRI, or may be independent of an MRI) configured to surround a body. A feedback mechanism, based on MRI image analysis, determines the current location of the nano-actuators, and the required current for the coils, which determines the strength and direction of the magnetic field at the specific location for the next step. For the coil orientation and currents, the 3D magnetic fields can be obtains, for example using ANSYS® simulations. This pre-calculated data is used for implementing the next state of currents in each coil. In a particular embodiment, the orientation and direction of motion of the nano-actuators may be controlled using a simple joystick control, which is configured to adjust the coil currents.

The plurality of deployed nano-actuators 100, 100' are magnetically propelled or navigated to the target cells 95. Propelling the plurality of nano-actuators towards the malignant cells may be accomplished by applying at least one of a gradient magnetic field and a rotating magnetic field. When the ligands applied to the nano-actuators 100, 100' encounter the target binding receptors on the target cells, the nano-actuator 100, 100' will engage the target cells. Depending on the selected ligand, the nano-actuator 100, 100' may thereby become attached to the membrane of the target cell, or may enter the cell. When the nano-actuators 100, 100' have had enough time to find and engage a target cell, the system 92 generates an intermittent constant magnetic field H 96A, that is selected to cause the FSMA nano-actuators 100, 100' to contract and expand, thereby shaking or disrupting the target cells 95. Alternatively, or subsequently, a rotating magnetic field H 96B may be applied, to cause the nano-actuators 100, 100' to rotate about their respective axes. The magnetic fields may cycle the helical members 102 between an expanded state and a contracted state. The oscillating magnetic field preferably induces a phase change in the compliant helical elements 102, as discussed above. The nano-actuators 100, 100' (and applied magnetic field) are designed such that the mechanical action of the nano-actuators 100, 100' on the target cells produces sufficient damage to the target cells to initiate a programmed cell death, without inducing necrotic cell death.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nano-actuator comprising a first head portion formed from a ferromagnetic material and a helical portion extending from the head portion, the helical portion comprising a compliant ferromagnetic shape memory alloy, wherein the helical portion is configured to be elastically compressible by applying an external magnetic field, and to expand when the external magnetic field is removed.

2. The nano-actuator of claim 1, wherein at least the first head portion of the nano-actuator further comprises an oxide layer.

3. The nano-actuator of claim 1, wherein the first head portion comprises a tapered distal portion and a cylindrical proximal portion.

4. The nano-actuator of claim 1, wherein the ferromagnetic shape memory alloy comprises an alloy of iron and palladium.

5. The nano-actuator of claim 1, wherein the nano-actuator further comprises an oxide layer on the head portion and a ligand retained on the oxide layer, wherein the ligand is selected to bind with a target malignant cell.

6. The nano-actuator of claim 1, wherein the nano-actuator further comprises a second head portion formed from a ferromagnetic material and connected to the helical portion opposite the first head portion.

7. The nano-actuator of claim 6, wherein the second head portion has a bullet shape comprising a tapered portion and a cylindrical portion.

8. A method for a targeted treatment of malignant cells comprising:
providing a plurality of nano-actuators, wherein each of the plurality of nano-actuators comprises a compliant helical member formed from a ferromagnetic shape memory alloy;
applying a ligand on a surface of each of the plurality of nano-actuators, wherein the ligand is selected to bind with a receptor of the malignant cells;
injecting the plurality of nano-actuators into a body containing the malignant cells;
propelling the plurality of nano-actuators towards the malignant cells by applying at least one of a gradient magnetic field and a rotating magnetic field, wherein at least some of the plurality of nano-actuators bind to at least some of the malignant cells;
cycling the compliant helical members of the plurality of nano-actuators between an expanded state and a contracted state by applying an oscillating magnetic field, wherein the oscillating magnetic field induces a phase change in the compliant helical members.

9. The method of claim 8, wherein the ferromagnetic shape memory alloy comprises an iron-palladium alloy.

10. The method of claim 9, wherein the ferromagnetic shape memory alloy comprises $Fe_{70}Pd_{30}$.

11. The method of claim 8, wherein each of the plurality of nano-actuators further comprises a first head portion that is fixed to a first end of the helical member.

12. The method of claim 11, wherein the first head portion of the plurality of nano-actuators comprises iron, an iron alloy, or another ferromagnetic material.

13. The method of claim 11, wherein the first head portion of the plurality of nano-actuators comprises an iron-palladium alloy.

14. The method of claim 11, wherein at least the first head portion of the plurality of nano-actuators further comprises a biocompatible oxide layer.

15. The method of claim 11, wherein at least one of the plurality of nano-actuators further comprises a second head portion that is fixed to a second end of the helical member, the first and second head portions comprising iron covered by a biocompatible oxide layer.

16. The method of claim 11, wherein the first head portion has a bullet shape comprising a tapered portion and a cylindrical portion.

17. The method of claim 8, wherein propelling the plurality of nano-actuators towards the malignant cells comprises applying a rotating magnetic field configured to cause the plurality of nano-actuators to spin.

18. A nano-robotic system comprising:
a magnetic field generator configured to selectably and controllably generate an oscillating magnetic field, a gradient magnetic field, and a rotating magnetic field;
a controller functionally connected to the magnetic field generator and operable to control the magnetic fields produced by the magnetic field generator; and
a plurality of nano-actuators, each nano-actuator comprising a first head portion formed from a ferromagnetic material and a helical portion extending from the head portion, the helical portion comprising a compliant ferromagnetic shape memory alloy, wherein the helical portion is configured to be elastically compressible by an external magnetic field generated by the magnetic field generator, and to expand when the external magnetic field is removed.

19. The nano-robotic system of claim 18, wherein the oscillating magnetic field is configured to induce a martensitic phase transformation in the ferromagnetic shape memory alloy.

20. The nano-robotic system of claim 19, wherein the ferromagnetic shape memory alloy comprises an iron-palladium alloy.

* * * * *